US00PP13351P2

(12) United States Plant Patent
van Rijn

(10) Patent No.: US PP13,351 P2
(45) Date of Patent: Dec. 10, 2002

(54) ANTHURIUM PLANT NAMED 'VR 098'

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 09/968,321

(22) Filed: Sep. 30, 2001

(51) Int. Cl.[7] ..... A01H 5/00
(52) U.S. Cl. ..... Plt./367

(58) Field of Search ..... Plt./367

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Anthurium plant named 'VR 098', characterized by its upright and somewhat outwardly spreading plant habit; freely clumping growth habit; durable dark green leaves; dark pink-colored spathes with grayed red-colored spadices that are positioned above and beyond the foliage on strong and erect scapes; freely flowering habit; and good inflorescence longevity.

2 Drawing Sheets

BACKGROUND OF THE INVENTION

Botanical classification: *Anthurium andreanum.*
Variety denomination: 'VR 098'.

The present invention relates to a new and distinct cultivar of Anthurium plant, botanically known as *Anthurium andreanum*, and hereinafter referred to by the name 'VR 098'.

The new Anthurium is a product of a planned breeding program conducted by the Inventor in Schipluiden, The Netherlands. The objective of the program is to create and develop new freely clumping and freely flowering Anthurium cultivars with strong roots, dark green leaves, attractive spathe color, and good inflorescence longevity.

The new Anthurium originated from a cross by the Inventor on or about Sep. 28, 1995 of the Inventor's proprietary *Anthurium andreanum* selection code number 90-41 as the female, or seed, parent with the Inventor's proprietary *Anthurium andreanum* selection code number 90-28 as the male, or pollen, parent. The cultivar VR 098 was discovered and selected by the Inventor as a plant within the progeny of the stated cross in a controlled environment in Schipluiden, The Netherlands in 1998.

Asexual propagation of the new cultivar by meristem culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar VR 098. These characteristics in combination distinguish 'VR 098' as a new and distinct cultivar:

1. Upright and somewhat outwardly spreading plant habit.
2. Freely clumping growth habit.
3. Durable dark green leaves.

4. Dark pink-colored spathes with grayed red-colored spadices that are positioned above and beyond the foliage on strong and erect scapes.
5. Freely flowering habit.
6. Good inflorescence longevity.

Plants of the new Anthurium can be compared to plants of the female parent, the selection 90-41. In side-by-side comparisons conducted in Schipluiden, The Netherlands, plants of the new Anthurium differed from plants of the selection 90-41 in the following characteristics:

1. Plants of the new Anthurium had a stronger growth habit than plants of the selection 90-41.
2. Plants of the new Anthurium had larger and more durable leaves than plants of the selection 90-41.
3. Spathe color of plants of the new Anthuriums was darker pink than spathe color of plants of the selection 90-41.

Plants of the new Anthurium can be compared to plants of the male parent, the selection 90-28. In side-by-side comparisons conducted in Schipluiden, The Netherlands, plants of the new Anthurium differed from plants of the selection 90-28 in the following characteristics:

1. Plants of the new Anthurium were bushier than plants of the selection 90-28.
2. Leaves of plants of the new Anthurium were lighter green in color than leaves of plants of the selection 90-28.
3. Spathe color of plants of the new Anthuriums was lighter pink than spathe color of plants of the selection 90-28.

Plants of the new Anthurium can be compared to plants of the cultivar Anouk, U.S. Plant patent application Ser. No. 09/968,320, filed concurrently with this application. In side-by-side comparisons conducted in Schipluiden, The Netherlands, plants of the new Anthurium differed from plants of the cultivar Anouk in the following characteristics:

1. Plants of the new Anthurium were not as compact as plants of the cultivar Anouk.
2. Plants of the new Anthurium had larger leaves than plants of the cultivar Anouk.
3. Plants of the new Anthurium had larger spathes than plants of the cultivar Anouk.

Plants of the new Anthurium can also be compared to plants of the cultivar Rapido, not patented. In side-by-side comparisons conducted in Schipluiden, The Netherlands, plants of the new Anthurium differed from plants of the cultivar Rapido in the following characteristics:

1. Plants of the new Anthurium had larger and more durable leaves than plants of the cultivar Rapido.

2. Plants of the new Anthurium had narrower and smaller spathes than plants of the cultivar Rapido.

3. Spathe color of plants of the new Anthurium were lighter pink than spathe color of plants of the cultivar Rapido.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the culitvar VR 098 that was about three years old.

The photograph at the top of the second sheet comprises a close-up view of a typical inflorescence of 'VR 098'.

The photograph at the bottom of the second sheet comprises a close-up view of the upper surface of a typical mature leaf of 'VR 098'.

DETAILED BOTANICAL DESCRIPTION

In the following description, color references are made to The Royal Horticultural Society Colour Chart, 1995 edition, except where general terms of ordinary dictionary significance are used. The following observations and measurements describe three-year old plants grown in 17-cm containers in Schipluiden, The Netherlands, in a glass greenhouse with an average day temperature of 25° C. and an average night temperature of 19° C.

Botanical classification: *Anthurium andreanum* cultivar VR 098.

Parentage:

*Female parent.*—Inventor's proprietary *Anthurium andreanum* selection code number 90-41, not patented.

*Male parent.*—Inventor's proprietary *Anthurium andreanum* selection code number 90-28, not patented.

Propagation:

*Method.*—By meristem culture.

*Time to develop roots on a meristem-cultured plant.*—Summer: About 70 days at 24° C. Winter: About 84 days at 21° C.

*Root description.*—Strong fleshy roots.

Plant description:

*Plant shape.*—Upright and somewhat outwardly spreading plant habit, inverted triangle, symmetrical.

*Growth habit.*—Freely clumping, bushy and dense growth habit. Appropriate for 17 to 35-cm containers. Vigorous.

*Plant height.*—About 90 to 110 cm.

*Plant diameter or spread.*—About 100 cm.

*Crop time.*—About 10 months are usually required from planting of young plants to finished plants in a 17-cm container.

*Foliage description.*—Quantity per plant: More than 100. Length: About 25 to 40 cm. Width: About 20 to 30 cm. Shape: Cordate. Apex: Apiculate. Base: Cordate. Margin: Entire. Texture: Leather; glabrous. Venation pattern: Pinnate. Color: Young leaves, upper surface: 147A. Young leaves, lower surface: 147B. Mature leaves, upper surface: Darker than 147A. Mature leaves, lower surface: 146A. Venation, upper surface: 148A. Venation, lower surface: 146C. Petiole: Length: About 30 to 60 cm. Color: 146D. Geniculum length: About 2 to 3 cm. Geniculum color: 146D.

Inflorescence description:

*Inflorescence arrangement.*—Spathes with spadices held above and beyond the foliage. Flowering structures arise from leaf axils. Freely and continuous flowering year-round; typically more than 25 inflorescences per plant at one time.

*Inflorescence longevity.*—Inflorescences last about six weeks under winter conditions and about three months under summer conditions; persistent.

*Spathe.*—Length: About 12 to 16 cm. Width: About 7 to 10 cm. Shape: Roughly ovate. Apex: Apiculate to mucronulate. Base: Truncate. Margin: Entire. Texture: Leathery; glabrous. Color: When opening, front and back surfaces: 60B; glossy. Fully developed, front surface: 51C; glossy. Fully opened, back surface: 55B, overlain with 143A blush; glossy.

*Spadix.*—Length: About 8 to 12 cm. Diameter: About 1.7 cm. Shape: Columnar. Cross section: Rounded. Longitudinal axis: Erect. Color: Immature: 79A. Mature: 182B.

*Flowers.*—Quantity per spadix: Numerous, about 400. Shape: Rounded. Diameter: About 1 mm, maximum.

*Reproductive organs.*—Androecium: Pollen color: Close to 20A. Gynoecium: Stigma shape: Ovoid.

*Scape.*—Length: About 60 to 80 cm. Aspect: Strong and erect. Color: 181A.

*Seed/fruit.*—Seed/fruit development on plants of the new Anthurium has not been observed to date.

Disease/pest resistance: Under commercial conditions, plants of the new Anthurium have not been observed to be resistant to pathogens or pests common to Anthurium.

It is claimed:

1. A new and distinct cultivar of Anthurium plant named 'VR 098', as illustrated and described.

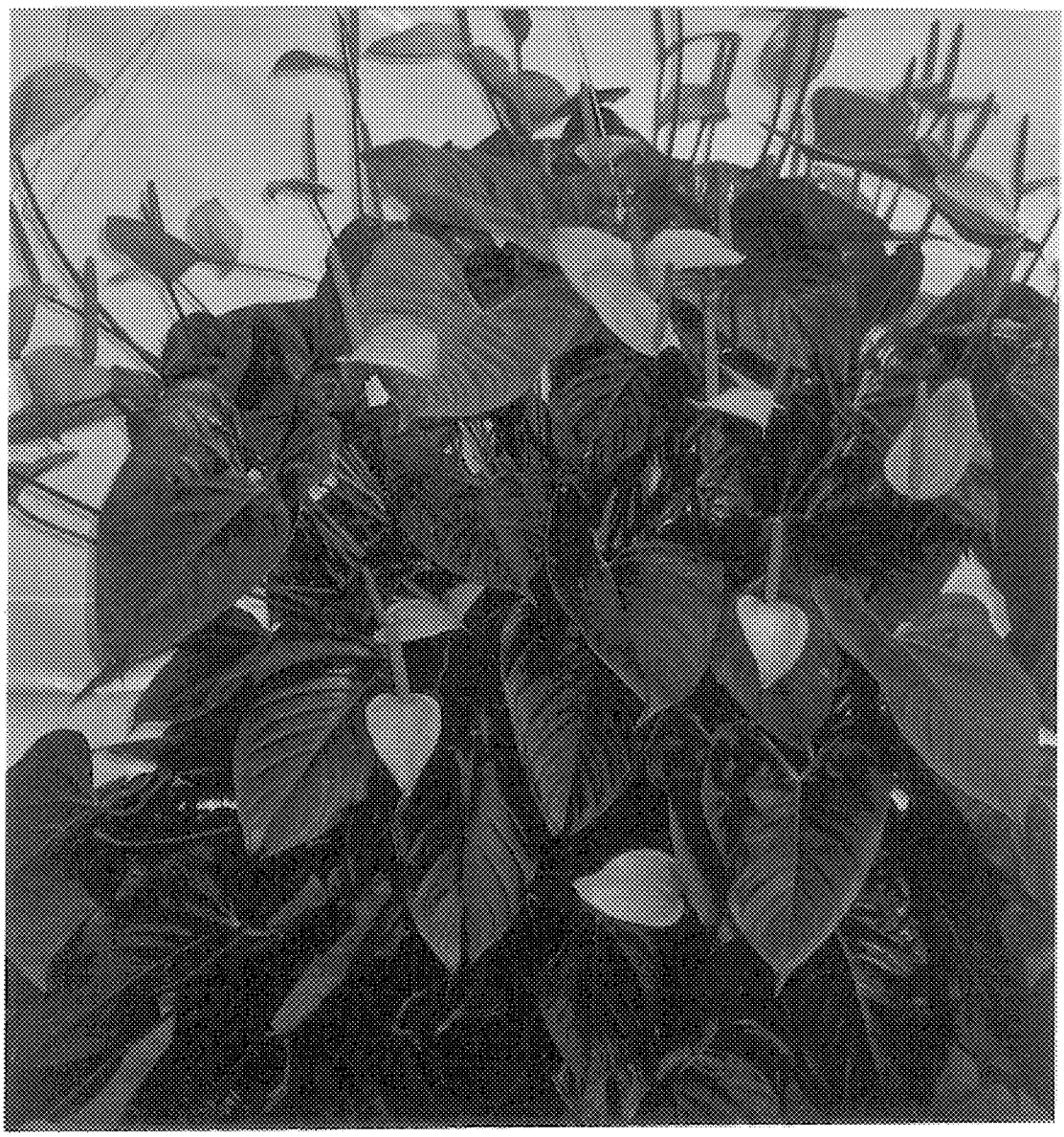

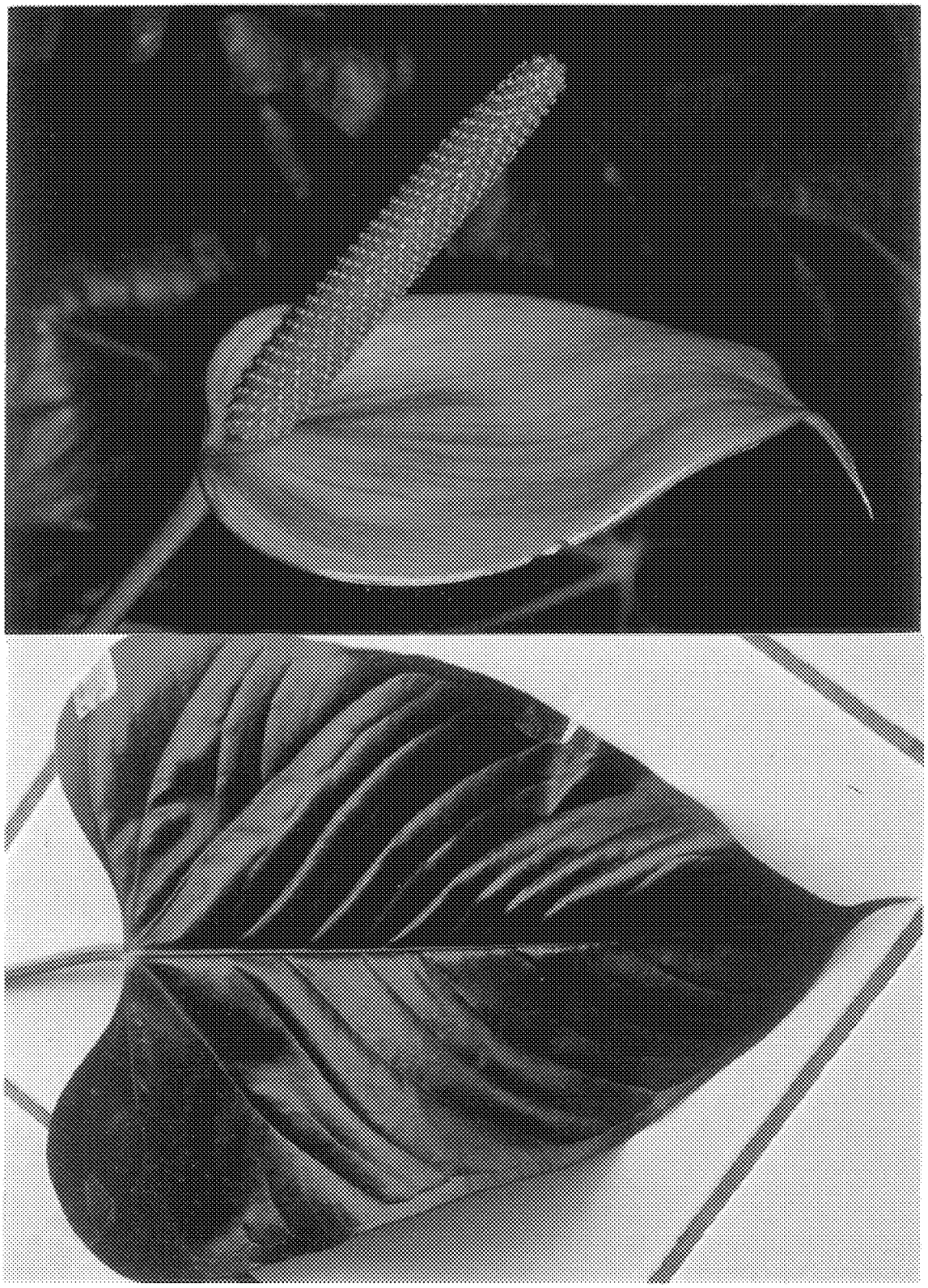

* * * * *